(12) United States Patent
Garcia Gonzalez et al.

(10) Patent No.: US 8,501,943 B2
(45) Date of Patent: Aug. 6, 2013

(54) SODIUM SALT OF 5-CYCLOPROPYL-2-{[2-(2,6-DIFLUORO-PHENYL)PYRIMIDIN-5-YL]AMINO}BENZOIC ACID AS DHODH INHIBITOR

(75) Inventors: Nuria Garcia Gonzalez, Barcelona (ES); Francesc Carrera Carrera, Barcelona (ES); Monserrat Julia Jane, Barcelona (ES); Laurent Debethune, Barcelona (ES); Xavier Serra Masia, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 13/256,127

(22) PCT Filed: Mar. 11, 2010

(86) PCT No.: PCT/EP2010/001548
§ 371 (c)(1),
(2), (4) Date: Sep. 19, 2011

(87) PCT Pub. No.: WO2010/102824
PCT Pub. Date: Sep. 16, 2010

(65) Prior Publication Data
US 2012/0003184 A1   Jan. 5, 2012

(30) Foreign Application Priority Data
Mar. 13, 2009  (EP) .................................. 09382033

(51) Int. Cl.
*A61K 31/505*  (2006.01)
(52) U.S. Cl.
USPC ..... 544/322; 544/131; 424/145.1; 424/144.1; 514/256; 514/217.04; 514/249; 514/352; 514/340; 546/312; 546/269.1; 546/257; 546/167; 546/194

(58) Field of Classification Search
USPC .................. 544/322, 131; 424/145.1, 144.1; 514/256, 217.04, 249, 352, 340; 546/312, 546/269.1, 257, 167, 194
See application file for complete search history.

(56) References Cited

U.S. PATENT DOCUMENTS

| | | |
|---|---|---|
| 5,780,592 A | 7/1998 | Müllner et al. |
| 7,071,222 B2 | 7/2006 | Bartlett et al. |
| 7,258,118 B2 | 8/2007 | Goede et al. |
| 8,258,308 B2 | 9/2012 | Castro Palomino Laria et al. |
| 2003/0004171 A1 | 1/2003 | Humphrey et al. |
| 2006/0081246 A1 | 4/2006 | Goede et al. |
| 2010/0074898 A1 | 3/2010 | Castro Palomino Laria et al. |

(Continued)

FOREIGN PATENT DOCUMENTS
EP  0 780 128  6/1997
WO  WO 97/34600  1/1997

(Continued)

OTHER PUBLICATIONS

Morissette et al. Advanced Drug Delivery Reviews 2004, 56, 275-300.*

(Continued)

*Primary Examiner* — Savitha Rao
(74) *Attorney, Agent, or Firm* — Finnegan, Henderson, Farabow, Garrett & Dunner, LLP

(57) ABSTRACT

The present disclosure is directed to the sodium salt of 5-cyclopropyl-2-{[2-(2,6-difluorophenyl)pyrimidin-5-yl]amino}benzoic acid, pharmaceutically acceptable solvates thereof, pharmaceutical combinations thereof, and methods of treatment.

5 Claims, 3 Drawing Sheets

(56) References Cited

U.S. PATENT DOCUMENTS

| | | |
|---|---|---|
| 2011/0129445 A1 | 6/2011 | Godessart Marina et al. |
| 2011/0212945 A1 | 9/2011 | Castro Palomino Laria et al. |
| 2011/0280831 A1 | 11/2011 | Godessart Marina et al. |
| 2012/0003183 A1 | 1/2012 | Garcia Gonzalez et al. |
| 2012/0014918 A1 | 1/2012 | Perez Garcia et al. |
| 2012/0245359 A1 | 9/2012 | Boix Bernardini |

FOREIGN PATENT DOCUMENTS

| | | |
|---|---|---|
| WO | WO 97/00703 | 9/1997 |
| WO | WO 99/45926 | 9/1999 |
| WO | WO 00/76489 | 12/2000 |
| WO | WO 02/080897 | 10/2002 |
| WO | WO 03/000325 | 1/2003 |
| WO | WO 03/006425 | 1/2003 |
| WO | WO 03/061742 | 7/2003 |
| WO | WO 2004/048314 | 6/2004 |
| WO | WO 2004/056746 | 7/2004 |
| WO | WO 2004/056747 | 7/2004 |
| WO | WO 2005/075410 | 8/2005 |
| WO | WO 2006/001961 | 1/2006 |
| WO | WO 2006/022442 | 3/2006 |
| WO | WO 2006/044741 | 4/2006 |
| WO | WO 2006/122788 | 11/2006 |
| WO | WO 2008/077639 | 7/2008 |
| WO | WO 2008/097180 | 8/2008 |
| WO | WO 2009/021696 | 2/2009 |
| WO | WO 2009/021696 A1 | 2/2009 |
| WO | WO 2009/153043 | 12/2009 |
| WO | WO 2010/083975 | 7/2010 |
| WO | WO 2010/102825 | 9/2010 |
| WO | WO 2010/102826 | 9/2010 |
| WO | WO 2011/045059 | 4/2011 |

OTHER PUBLICATIONS

Vippagunta, Sudha R. "Crystalline Solids." Advanced Drug Delivery Reviews 48(2001): 3-26.*
Ando et al. (Remington, 20th edition, 2000, pp. 704-712.*
International Search Report for International Application No. PCT/EP2010/001548 mailed Sep. 21, 2010.
Batt, Douglas G., "Inhibitors of dihydroorotate dehydrogenase", *Exp. Opin. Ther. Patents* 9(1):41-54, 1999.
Phillips, Margaret A. et al., "Triazolopyrimidine-Based Dihydroorotate Dehydrogenase Inhibitors with Potent and Selective Activity Against the Malaria Parasite *Plasmodium falciparum*", *J. Med. Chem.*, 51, 3649-3653, 2008.
Vyas, V.K. et al., "Recent Developments in the Medicinal Chemistry and Therapeutic Potential of Dihydroorotate Dehydrogenase (DHODH) Inhibitors", *Mini-Reviews in Medicinal Chemistry*, 11, 1039-1055, 2011.
Cutolo, M. et al., "Anti-inflammatory mechanisms of methotrexate in rheumatoid arthritis," Ann. Rheum. Dis. (2001) 60:729-735.
Grigoreva, "Catalytic Activity," Khimiko-Farmatsevticheskii Zhurnal (1978) 12(4):7-18.
English translation of Grigoreva, "Catalytic Activity," Khimiko-Farmatsevticheskii Zhurnal (1978) 12(4):7-18.
International Search Report mailed Nov. 12, 2010, for International Application No. PCT/EP2010/006283 (WO 2011/045059).
Kermack, W.O. and Weatherhead, A.P., "Some Anilinopyridine Derivatives," Journal of the Chemical Society (1942) pp. 726-727.
Notice of Allowance dated May 2, 2012, in U.S. Appl. No. 12/520,237.
Notice of Allowability (Corrected) dated Jun. 26, 2012, in U.S. Appl. No. 12/520,237.
Office Action (Restriction Requirement) dated Sep. 13, 2012, in U.S. Appl. No. 13/145,628.
Office Action dated Sep. 28, 2012, in U.S. Appl. No. 12/999,698.
Office Action dated Feb. 28, 2011, in U.S. Appl. No. 12/520,237.
Office Action (Restriction Requirement) dated Jun. 12, 2012, in U.S. Appl. No. 12/672,725.
Office Action (Restriction Requirement) dated Jun. 4, 2012, in U.S. Appl. No. 12/999,698.
Office Action dated Jul. 30, 2012, in U.S. Appl. No. 12/672,725.
Office Action (Restriction Requirement) dated Apr. 2, 2013, in U.S. Appl. No. 13/567,437.
Office Action (Restriction Requirement) dated Apr. 12, 2013, in U.S. Appl. No. 12/256,349.
Patani, G.A. and Lavoie, E.M., "Bioisosterism: A Rational Approach in Drug Design," Chem. Rev. (1996) 96:3147-3176.
Silverman, R.B., "The Organic Chemistry of Drug Design and Drug Action," Section 2.1, pp. 9, Elsevier Academic Press (2004).
Wahl, C. et al,. "Sulfasalazine: a Potent and Specific Inhibitor of Nuclear Factor Kappa B," J. Clin. Invest., 101(5): 1163-1174 (1998).
Bastin, R.J. et al., "Salt Selection and Optimisation Procedures for Pharmaceutical New Chemical Entities" Organic Process Research & Development (2000) 4:427-435.
U.S. Appl. No. 12/520,237, filed Sep. 9, 2009, Castro Palomino Laria et al.
U.S. Appl. No. 12/672,725, filed Mar. 16, 2010, Castro Palomino Laria et al.
U.S. Appl. No. 12/999,698, filed Dec. 17, 2010, Godessart Marina et al.
U.S. Appl. No. 13/145,628, filed Jul. 21, 2011, Godessart Marina et al.
U.S. Appl. No. 13/256,104, filed Sep. 19, 2011, Garcia Gonzalez et al.
U.S. Appl. No. 13/256,349, filed Sep. 13, 2011, Perez Garcia et al.
Baughman, RP et al. "Leflunomide for Chronic Sarcoidosis," *Clinical Research*, 21: 43-48 (2004).
Berge, S.M. et al., "Pharmaceutical Salts", *Journal of Pharmaceutical Science*, American Pharmaceutical Association, Washington, DC, vol. 66, No. 1, Jan. 1, 1977, pp. 1-19, XP000562636, ISSN: 0022-3549.
Breedveld, FC et al. "Leflunomide: Mode of Action in the Treatment of Rheumatoid Arthritis," *Annals of the Rheumatic Diseases*, 59: 841-849 (2000).
ClinialTrials.gov Identifier: NCT00637819, Sanofi-Aventis, Double blind, randomized, placebo controlled pilot study of leflunomide in systemic lupus erythematosus (SLE) (2008).
Dexter, DL et al. "Activity of a Novel 4-Quinolinecarboxylic Acid, NSC 368390 [6-Fluoro-2-(2'-fluoro-1,1'-biphenyl-4-yl)-3-methyl-4-quinolinecarboxylic Acid Sodium Salt], against Experimental Tumors," *Cancer Research*, 45: 5563-5568 (Nov. 1985).
Dimitrova, P. et al. "Restriction of De Novo Primidine Biosynthesis Inhibits Th1 Cell Activation and Promotes Th2 Cell Differentiation," *The Journal of Immunology*, 169:3392-3399 (2002).
English-language Derwent Abstract for WO 06/022442, Mar. 2, 2006.
English Language Caplus Abstract for Spano, R. et al. "Preparation and pharmacology of some derivatives of 2-aminonicotinic," *Farmaco, Edizione Scientifica*, Societa Chimica Italiana, Pavia, IT, 26(9): 844-849 (1971).
Fox, RI "Mechanism of Action of Leflunomide in Rheumatoid Arthritis," *The Journal of Rheumatology*, 25, Supplement 53:20-26 (1998).
Gu, L. et al., "Preformulation Salt Selection. Physical Property Comparisons of the Tris (Hydroxymethyl) Aminomethane (THAM) Salts of Four Analgesic/Anti-inflammatory Agents with the Sodium Salts and the Free Acids," Pharmaceutical Research, Kluwer Academic Publishers, New York, NY, vol. 4, No. 3, Jan. 1, 1987, pp. 255-257, XP002099348, ISSN: 0724-8741.
Haibel, J. et al. "Six Month Open Label Trial of Leflunomide in Active Ankylosing Spondylitis," *Annals of the Rheumatic Diseases*, 64: 124-126 (2005).
International Search Report mailed May 8, 2008, for International Application No. PCT/EP2007/011401 (WO 2008/077639 A1).
International Search Report mailed Oct. 20, 2008, for International Application No. PCT/EP2008/006573 (WO 2009/021696).
International Search Report mailed Jul. 31, 2009, for International Application No. PCT/EP2009/004404 (WO 2009/153043).
International Search Report mailed Apr. 16, 2010, for International Application No. PCT/EP2010/000270 (WO 2010/083975).
International Search Report for International Application No. PCT/EP2010/001549 dated May 31, 2010.

International Search Report for International Application No. PCT/EP2010/001550 mailed Apr. 23, 2010.

John, GT et al. "Leflunomide Therapy For Cytomegalovirus Disease in Renal Allograft Recipients," *Transplantation*, 77(9): 1460-1461 (2003).

Kremer, JM "Concomitant Leflunomide Therapy in Patients with Active Rheumatoid Arthritis despite Stable Doses of Methotrexate," Annals of Internal Medicine, 137(9): 726-733 (2002).

Kremer, JM "Methotrexate and leflunomide: Biochemical basis for combination therapy in the treatment of rheumatoid arthritis," Seminars in Arthritis and Rheumatism, 29(1): 14-26 (1999).

Kulkarni, OP et al. "4SC-101, A Novel Small Molecule Dihydroorotate Dehydrogenase Inhibitor, Suppresses Systemic Lupus Erythematosus in MRL-(Fas)lpr Mice," The American Journal of Pathology, 176(6): 2840-2847 (2010).

Leban, J. et al. "Biphenyl-4-ylcarbamoyl thiophene carboxylic acids as potent DHODH inhibitors," Bioorganic & Medicinal Chemistry Letters, 16(2): 267-270 (2006).

Liu, S. et al. "Structures of Human Dihydroorotate Dehydrogenase in Complex with Antiproliferative Agents," *Structure*, 8(1): 25-33 (2000).

Löffler, M. et al. "Dihydroorotat-ubiquinone oxidoreductase links mitochondria in the biosynthesis of pyrimidine nucleotides," *Molecular and Cellular Biochemistry*, 174: 125-129 (1997).

Majithia, V. et al. "Successful Treatment of Sarcoidosis with Leflunomide," Rheumatology, 42: 700-702 (2003).

Manna, SK et al. "Leflunomide Suppresses TNF-Induced Cellular Responses: Effects on NF-{kappa}B, Activator Protein-1, c-Jun N-Terminal Protein Kinase, and Apoptosis," *Journal of Immunology*, 165:5962-5969 (2000).

McRobert, L. et al. "RNA Interference (RNAi) Inhibits Growth of *Plasmodium falciparum*," *Molecular & Biochemical Parasitology*, 19: 273-278 (2002).

Mehta, V. et al. "Leflunomide," Indian J. Dermatol. Venereol. Leprol., 75(4): 422-425 (2009).

Metzler, C. et al. "Maintenance of Remission with Leflunomide in Wegener's Granulomatosis," *Rheumatology*, 43:315-320 (2004).

Miyaura, N. et al. "Palladium-Catalyzed Cross-Coupling Reactions of Organoboron Compounds," *Chemical Reviews*, 35:2457-2483 (1995).

O'Connor, PW et al. "A Phase II Study of the Safety and Efficacy of Teriflunomide in Multiple Sclerosis with Relapses," *Neurology*, 66:894-900 (2006).

Office Action dated Jun. 2, 2011, in U.S. Appl. No. 12/520,237.

Office Action dated Nov. 4, 2011, in U.S. Appl. No. 12/520,237.

Patani, GA et al. "Bioisosterism: A Rational Approach in Drug Design," Chem. Rev. 96: 314-3176 (1996).

Sanders, S. et al. "Leflunomide for the Treatment of Rheumatoid Arthritis and Autoimmunity," American Journal of the Medical Sciences, 323(4): 190-193 (2002).

Schläpfer, E. et al. "Anti-HIV-1 Activity of Leflunomide: a Comparison with Mycophenolic Acid and Hydroxyurea," *AIDS*, 17(11): 1613-1620 (2003).

Silverman, E. et al. "Long-Term Open-Label Preliminary Study of the Safety and Efficacy of Leflunomide in Patients with Polyarticular-Course Juvenile Rheumatoid Arthritis," *Arthritis & Rheumatism*, 52(2): 554-562 (2005).

Silverman, RB "The Organic Chemistry of Drug Design and Drug Action," Chapter 2, Section 2.2, pp. 29-32, Elsevier Academic Press (2004).

Spano, R. et al. "Preparation and pharmacology of some derivatives of 2-aminonicotinic," Farmaco, Edizione Scientifica, Societe Chimica Italiana, Pavia, IT, 26(9): 844-849 (1971).

Stahl, P.H. et al., "Tromethamine", Handbook of Pharmaceutical Salts Properties, Selection and Use, Jan. 1, 2002, pp. 324-325.

Tlacuilo Parra, JA et al. "Leflunomide in the treatment of psoriasis: results of a phase II open trial," British Journal of Dermatology, 150: 970-976 (2004).

Urushibara, M. et al. "The Antirheumatic Drug Leflunomide Inhibits Osteoclastogenesis by Interfering With Receptor Activator of NF-$_K$B Ligand-Stimulated Induction of Nuclear Factor of Activated T Cells c1," *Arthritis & Rheumatism*, 50(3): 794-804 (2004).

Weinblatt, ME et al. "Pharmacokinetics, safety, and efficacy of combination treatment with methotrexate and leflunomide in patients with active rheumatoid arthritis," *Arthritis & Rheumatism*, 42(7): 1322-1328 (Jul. 1999).

* cited by examiner

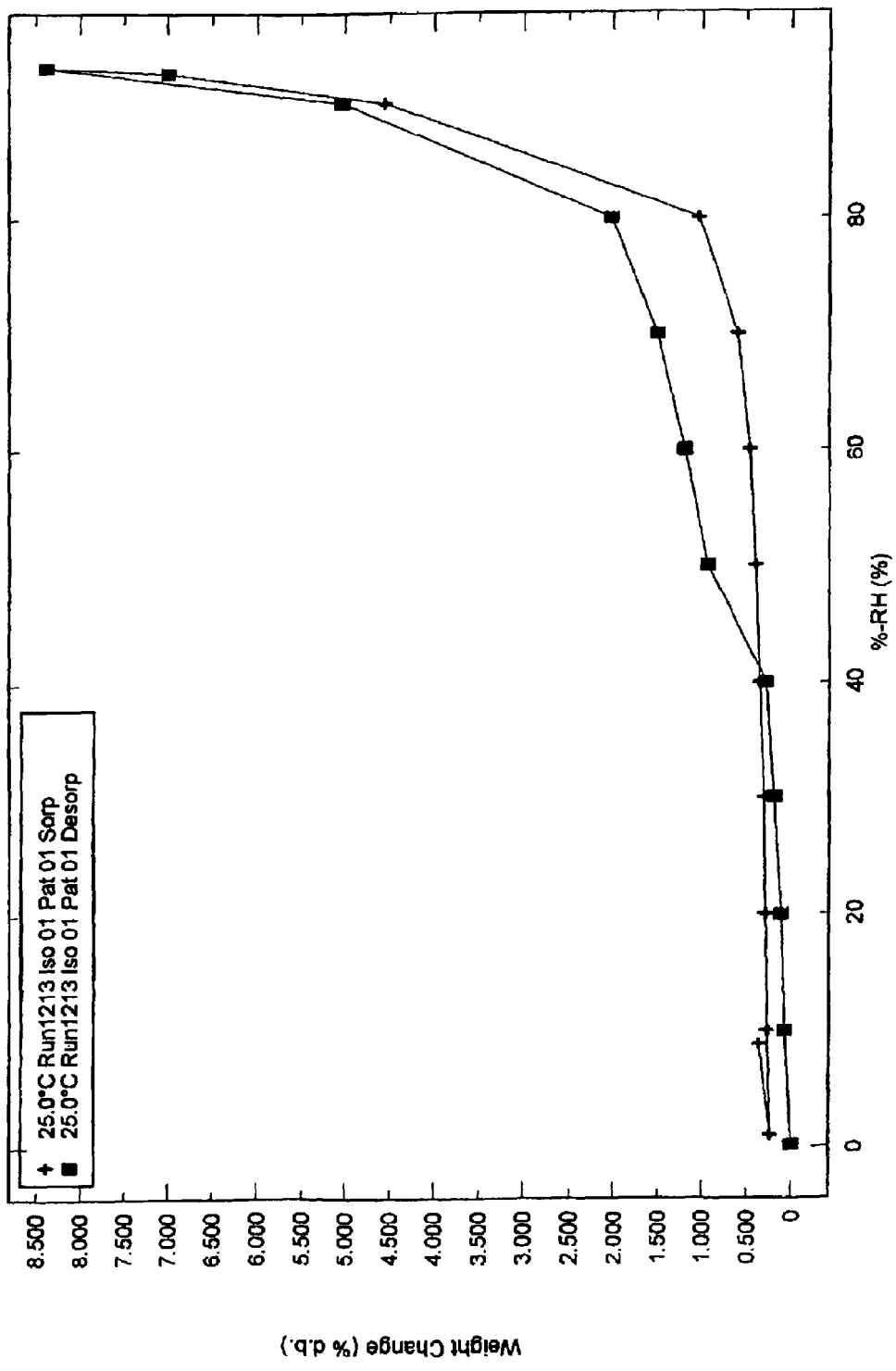

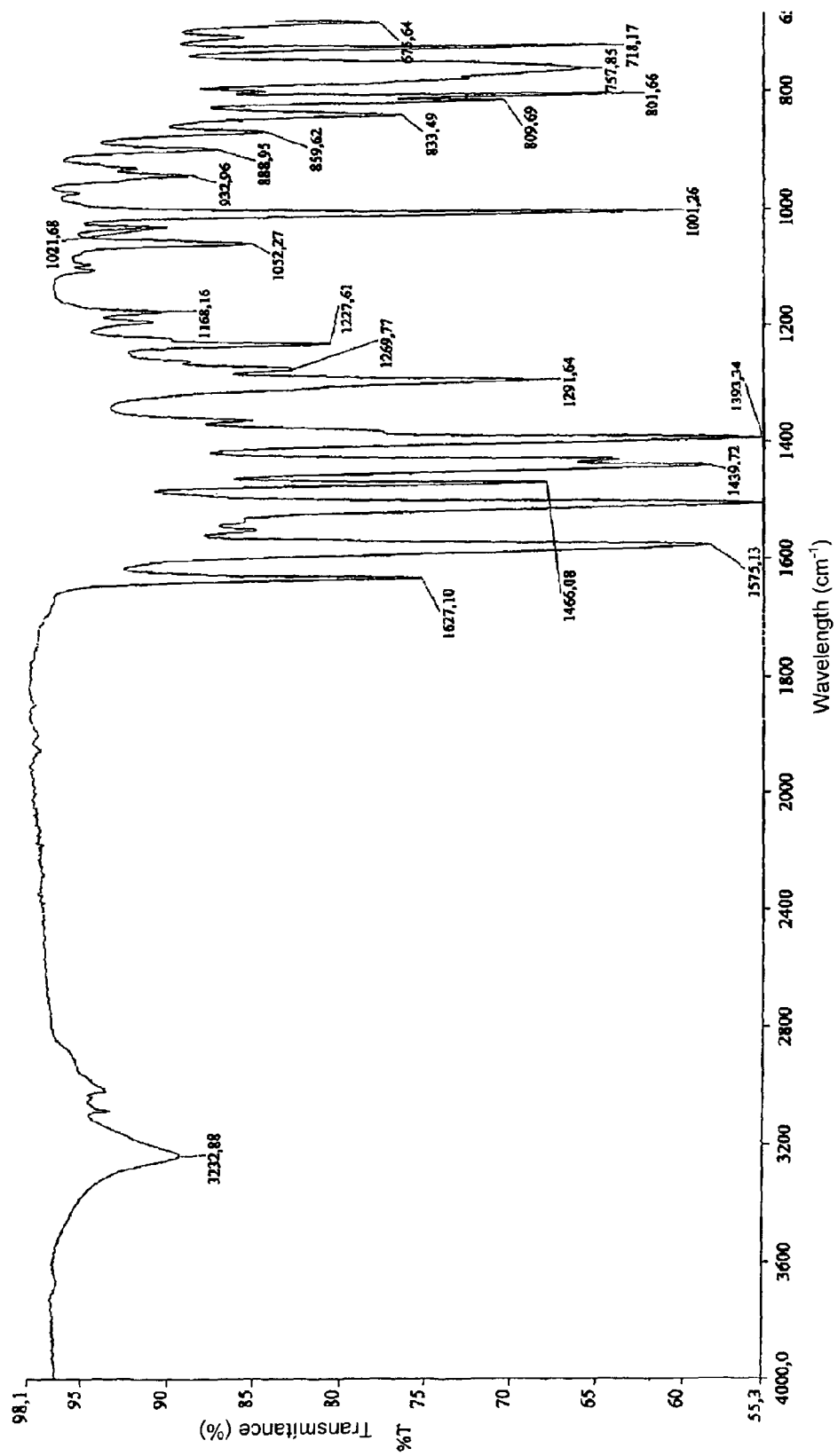

SODIUM SALT OF 5-CYCLOPROPYL-2-{[2-(2,6-DIFLUOROPHENYL)PYRIMIDIN-5-YL]AMINO}BENZOIC ACID AS DHODH INHIBITOR

This application is a national stage entry under 35 U.S.C. §371 of International Application No. PCT/EP2010/001548 filed on Mar. 11, 2010, which claims priority of European Patent Application No. 09382033.0, filed on Mar. 13, 2009. The contents of both applications are incorporated herein by reference.

FIELD OF THE INVENTION

The present invention is directed to the water-soluble crystalline sodium salt of 5-cyclopropyl-2-{[2-(2,6-difluorophenyl)pyrimidin-5-yl]amino}benzoic acid and solvates thereof. The invention is also directed to pharmaceutical compositions comprising the salt, methods of using it to treat, prevent or suppress diseases and disorders susceptible to be ameliorated by inhibition of dihydroorotate dehydrogenase, and processes and intermediates useful for preparing such salt.

BACKGROUND OF THE INVENTION

Dihydroorotate dehydrogenase (DHODH) inhibitors are compounds useful in the treatment, prevention or suppression of diseases and disorders known to be susceptible to improvement by inhibition of dihydroorotate dehydrogenase, such as autoimmune diseases, immune and inflammatory diseases, destructive bone disorders, malignant neoplastic diseases, angiogenic-related disorders, viral diseases, and infectious diseases.

In view of the physiological effects mediated by inhibition of dihydroorotate dehydrogenase, several DHODH inhibitors have been recently disclosed for the treatment or prevention of the diseases or disorders indicated above. See for example, WO2006/044741; WO2006/022442; WO2006/001961, WO2004/056747, WO2004/056746, WO2003/006425, WO2002/080897 and WO99/45926.

One of the most challenging tasks for formulators in the pharmaceutical industry is incorporating poorly water-soluble drugs into effective pharmaceutical compositions intended for parenteral, e.g. intravenous, or oral administration.

Additionally, the aqueous solubility of poorly water-soluble drugs is an important factor affecting their bioavailability. Improving the solubility of these poorly water-soluble drugs may be achieved using a number of different systems (emulsions, microemulsions, self-emulsifying or micronization). However, all of these systems may need the presence of surfactants to solubilize or emulsify the drugs.

The solubility of poorly water-soluble drugs might also be improved by preparing their addition salts. However, in some cases unstable salts are formed due to hygroscopicity (the process by which a substance attracts moisture from the atmosphere by through either absorption or adsorption) or deliquescence (the process by which a substance absorbs moisture from the atmosphere until it dissolves in the absorbed water and forms a solution)

WO2009/021696 discloses 5-cyclopropyl-2-{[2-(2,6-difluorophenyl)pyrimidin-5-yl]amino}benzoic acid and other azabiphenylaminobenzoic acid derivatives as potent DHODH inhibitors. Although this compound has shown adequate pharmacological activity, it is poorly water soluble.

Accordingly, there is a need for water soluble DHODH inhibitors, which are also soluble in the gastrointestinal pH range, and in a physically and chemically stable, non-deliquescent form with acceptable levels of hygroscopicity and relative high melting point. This would allow the material to be further manipulated, e.g. by micronization without significant decomposition, loss of crystallinity or exhibiting any change in polymorphism to prepare pharmaceutical compositions and formulations.

SUMMARY OF THE INVENTION

It has now been found that the sodium salt of 5-cyclopropyl-2-{[2-(2,6-difluorophenyl)pyrimidin-5-yl]amino}benzoic acid is water-soluble and can be obtained in a crystalline form which is neither hygroscopic nor deliquescent and which has a relatively high melting point.

Thus, the present invention provides a crystalline sodium salt of 5-cyclopropyl-2-{[2-(2,6-difluorophenyl)pyrimidin-5-yl]amino}benzoic acid and pharmaceutically acceptable solvates thereof.

The invention also provides a pharmaceutical composition comprising the salt of the invention and a pharmaceutically-acceptable carrier. The invention further provides combinations comprising the salt of the invention and one or more other therapeutic agents and pharmaceutical compositions comprising such combinations.

The invention also provides a method of treatment of a pathological condition or disease susceptible to amelioration by inhibition of dihydroorotate dehydrogenase, in particular wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis, comprising administering a therapeutically effective amount of the salt of the invention. The invention further provides a method of treatment comprising administering a therapeutically effective amount of a combination of the salt of the invention together with one or more other therapeutic agents or administering a therapeutically effective amount of a pharmaceutical composition comprising such combination.

The invention further provides synthetic processes and intermediates described herein, which are useful for preparing the salt of the invention.

The invention also provides the salt of the invention as described herein, a combination of the salt of the invention together with one or more other therapeutic agents or a pharmaceutical composition comprising such combination for use in the treatment of a pathological condition or disease susceptible to amelioration by inhibition of dihydroorotate dehydrogenase, in particular wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis. The invention also provides the use of the salt of the invention, a combination of the salt of the invention together with one or more other therapeutic agents or a pharmaceutical composition comprising such combination for the manufacture of a formulation or medicament for treating these diseases.

BRIEF DESCRIPTION OF FIGURES

FIG. 2 illustrates the DVS pattern of 5-cyclopropyl-2-{[2-(2,6-difluorophenyl)pyrimidin-5-yl]amino}benzoic acid, sodium salt.

FIG. 3 illustrates the IR spectra of 5-cyclopropyl-2-{[2-(2, 6-difluorophenyl)pyrimidin-5-yl]amino}benzoic acid, sodium salt.

DETAILED DESCRIPTION OF THE INVENTION

Figure 1:
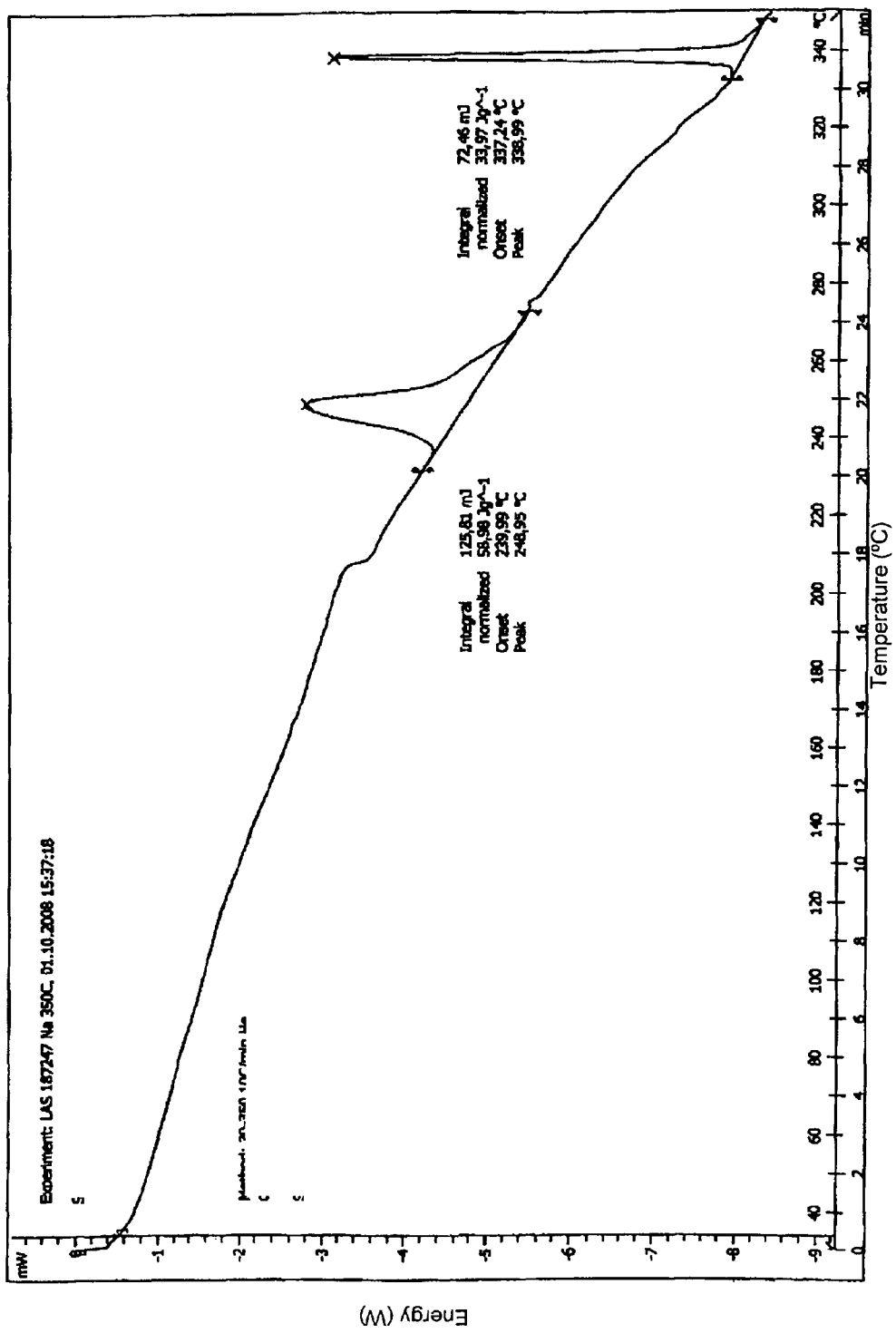
FIG. 1 illustrates the DSC thermogram of 5-cyclopropyl-2-{[2-(2,6-difluorophenyl)pyrimidin-5-yl]amino}benzoic acid, sodium salt.

When describing the salts, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:
(a) preventing the disease or medical condition from occurring, i.e., prophylactic treatment of a patient;
(b) ameliorating the disease or medical condition, i.e., causing regression of the disease or medical condition in a patient;
(c) suppressing the disease or medical condition, i.e., slowing the development of the disease or medical condition in a patient; or
(d) alleviating the symptoms of the disease or medical condition in a patient.

The term "solvate" refers to a complex or aggregate formed by one or more molecules of a solute, i.e. the salt of the invention or a pharmaceutically-acceptable salt thereof, and one or more molecules of a solvent. Such solvates are typically crystalline solids having a substantially fixed molar ratio of solute and solvent. Representative solvents include by way of example, water, ethanol, isopropanol and the like. When the solvent is water, the solvate formed is a hydrate.

Autoimmune diseases which may be prevented or treated include but are not limited to rheumatoid arthritis, psoriatic arthritis, systemic lupus erythematosus, multiple sclerosis, psoriasis, ankylosing spondylytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases which may be prevented or treated include but are not limited to asthma, COPD, respiratory distress syndrome, acute or chronic pancreatitis, graft versus-host disease, chronic sarcoidosis, transplant rejection, contact dermatitis, atopic dermatitis, allergic rhinitis, allergic conjunctivitis, Behcet syndrome, inflammatory eye conditions such as conjunctivitis and uveitis.

Destructive bone disorders which may be prevented or treated include but are not limited to osteoporosis, osteoarthritis and multiple myeloma-related bone disorder.

Malignant neoplastic diseases that may be prevented or treated include but are not limited to prostate, ovarian and brain cancer.

Angiogenesis-related disorders that may be prevented or treated include but are not limited to hemangiomas, ocular neovascularization, macular degeneration or diabetic retinopathy.

Viral diseases which may be prevented or treated include but are not limited to HIV infection, hepatitis and cytomegalovirus infection.

Infectious diseases which may be prevented or treated include but are not limited to sepsis, septic shock, endotoxic shock, Gram negative sepsis, toxic shock syndrome, Shigellosis and other protozoal infestations such as malaria.

Typically, the crystalline sodium salt of 5-cyclopropyl-2-{[2-(2,6-difluorophenyl)pyrimidin-5-yl]amino}benzoic acid corresponds to formula (I)

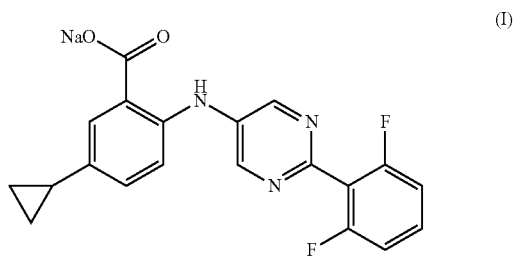

The invention also encompasses pharmaceutical compositions comprising a therapeutically effective amount of the salt as hereinabove defined and a pharmaceutically acceptable carrier.

In an embodiment of the present invention the pharmaceutical composition further comprises a therapeutically effective amount of one or more other therapeutic agents.

The invention is also directed to combinations comprising the salt of the invention and one or more other therapeutic agents and pharmaceutical compositions comprising such combinations.

The invention is also directed to the salt of the invention as described herein, a combination of the salt of the invention together with one or more other therapeutic agents or a pharmaceutical composition comprising such combination for use in the treatment of a pathological condition or disease susceptible to amelioration by inhibition of dihydroorotate dehydrogenase, in particular wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis. The invention also encompasses the use of the salt of the invention, a combination of the salt of the invention together with one or more other therapeutic agents or a pharmaceutical composition comprising such combination for the manufacture of a formulation or medicament for treating these diseases.

The invention also encompasses a method of treatment of a pathological condition or disease susceptible to amelioration by inhibition of dihydroorotate dehydrogenase, in particular wherein the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis, comprising administering a therapeutically effective amount of the salt of the invention. The invention also encompasses a method of treatment comprising administering a therapeutically effective amount of a combination of the salt of the invention together with one or more other therapeutic agents or administering a therapeutically effective amount of a pharmaceutical composition comprising such combination.

General Synthetic Procedures

The salt of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Processes for preparing the salt of the invention are provided as further embodiments of the invention and are illustrated by the procedures below.

The salt of the invention can be synthesized from 5-cyclopropyl-2-{[2-(2,6-difluorophenyl)pyrimidin-5-yl]amino}benzoic acid and from sodium hydroxide or from sodium methoxide, preferably from sodium hydroxide, which are commercially available from, for example, Scharlau.

Suitable inert diluents for this reaction include, but are not limited to, acetone, acetonitrile, ethyl acetate, chloroform, N,N-dimethylformamide, ethanol, isopropanol, nitromethane, dimethyl carbonate, methanol, methyl tert-butyl ether, tetrahydrofurane, diisopropyl ether, cyclohexane, butanol, water, 3-pentanone, toluene, chlorobenzene and isobutyl acetate and the like, and mixtures thereof, optionally containing water.

Upon completion of any of the foregoing reactions, the salt can be isolated from the reaction mixture by any conventional means such as precipitation, concentration, centrifugation and the like.

It will be appreciated that while specific process conditions (i.e. reaction temperatures, times, mole ratios of reactants, solvents, pressures, etc.) are given, other process conditions can also be used unless otherwise stated.

A water-soluble salt of the invention typically contains between about 0.85 and 1.15 molar equivalents of 5-cyclopropyl-2-{[2-(2,6-difluorophenyl)pyrimidin-5-yl]amino}benzoic acid per molar equivalent of the free base, more typically about 1 molar equivalent of 5-cyclopropyl-2-{[2-(2,6-difluorophenyl)pyrimidin-5-yl]amino}benzoic acid per molar equivalent of the free base.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

EXAMPLES

General. Reagents, starting materials, and solvents were purchased from commercial suppliers and used as received.

Crystallisation tests of salts of 5-cyclopropyl-2-{[2-(2,6-difluorophenyl)pyrimidin-5-yl]amino}benzoic acid with a broad range of pharmaceutically acceptable bases (comprising among others ammonia, L-arginine, choline, lysine, magnesium methoxide, meglumine, potassium methoxide and sodium hydroxide) in a range of different pharmaceutically acceptable solvents (including among others acetone, acetonitrile, ethyl acetate, chloroform, N,N-dimethylformamide, ethanol, isopropanol, nitromethane, dimethyl carbonate, methanol, methyl tert-butyl ether, tetrahydrofurane, diisopropyl ether, cyclohexane, butanol, water, 3-pentanone, toluene, chlorobenzene and isobutyl acetate) have been undertaken.

The salts from L-arginine, choline, magnesium methoxide and potassium methoxide were crystalline but hygroscopic. Additionally, some of said salts have different polymorphic phases. On the other hand, the salts from lysine and meglumine rendered either oils or amorphous solids. Finally, all the solids obtained with ammonia corresponded to the acid, suggesting a decomposition of the salt during the crystallization process.

Only the salt of the invention was neither hygroscopic nor deliquescent and had a relatively high melting point allowing it to be micronized and to have long term stability and presented no polymorphic phases.

Particularly good methods to prepare the salt of the invention are illustrated in the following examples.

The differential scanning calorimetry (DSC) thermograms analyses were obtained using a DSC-821 Mettler-Toledo instrument, serial number 5117423874. Samples were weighed into an aluminium pan, an aluminium lid placed on top of the sample and compressed with a brass rod. Samples were equilibrated at 30° C. and heated at 10° C./min to 350° C. The instrument was calibrated using indium and zinc standards.

Infrared spectroscopy (IR) spectra were obtained using a Perkin Elmer Spectrum One FT-IR instrument, serial number 70749, equipped with a universal ATR accessory. Solid samples were introduced directly into the ATR. The acquisition range was 650 to 4000 $cm^{-1}$.

Dynamic Vapour Sorption (DVS) profiles were obtained using an Igasorp Hiden Isochema instrument (serial number IGA-SA-066). After an initial stabilization period, at least two isotherms (at 25° C.) were obtained for each sample: a moisture sorption from 0 to 95% relative humidity and moisture desorption from 95% relative humidity to dryness. Both isotherms were performed in 10% humidity steps, with a minimum time of 10 minutes and a maximum time of 30 minutes for each step.

Example 1

Preparation of 5-cyclopropyl-2-{[2-(2,6-difluorophenyl)pyrimidin-5-yl]amino}benzoic acid, sodium salt A solution of sodium hydroxide (11.1 mg, 0.27 mmol) in methanol (0.2 mL) was added to a suspension of 5-cyclopropyl-2-{[2-(2,6-difluorophenyl)pyrimidin-5-yl]amino}benzoic acid (100 mg, 0.27 mmol) in 5 mL of isopropanol. The resulting solution was heated at reflux temperature (82° C.) for an hour, cooled to room temperature and stirred at 0° C. for 8 hours. The solid was filtered off, washed with cold isopropanol and dried under vacuum (5-7 mbar) at 100° C. for 4 h to give 0.092 g of the salt (yield 83%) as a pale yellow solid. Residual solvent: 1.6% of isopropanol.

FIG. 1 illustrates the DSC thermogram of the sodium salt of 5-cyclopropyl-2-{[2-(2,6-difluorophenyl)pyrimidin-5-yl]amino}benzoic acid. The sample exhibits a wide endotherm at onset 240° C. that likely corresponds to a crystalline transition and a narrow endotherm at onset 337° C. that probably corresponds to a melting of the salt. This indicates that the sample does not suffer any decomposition at low-medium temperatures, confirming thus its high stability.

FIG. 2 illustrates the DVS pattern of the sodium salt of 5-cyclopropyl-2-{[2-(2,6-difluorophenyl)pyrimidin-5-yl]amino}benzoic acid. Mass increase was measured at 80% (0.7% increase) and 90% (4.2% increase) relative humidity (RH). According to the results, said salt is not hygroscopic and exhibited no hysteresis.

FIG. 3 illustrates the IR spectra of the sodium salt of 5-cyclopropyl-2-{[2-(2,6-difluorophenyl)pyrimidin-5-yl]amino}benzoic acid. Characteristic signals appear at 3232, 1627, 1575, 1466, 1439, 1393, 1291, 1269, 1227, 1168, 1052, 1021, 1001, 932, 888, 859, 833, 809, 801, 757, 718 and 675 cm-1.

Water—Solubility Test:

The solubility of Example 1 in water at room temperature was determined together with the solubility of the corresponding free acids. The results are shown in Table 1 below.

| Ex. | Product | Water Solubility @ 25° C. (mg/mL as acid) |
|---|---|---|
| C1 | 5-cyclopropyl-2-{[2-(2,6-difluorophenyl)pyrimidin-5-yl]amino}benzoic acid | 0.03 |
| Ex. 1 | 5-cyclopropyl-2-{[2-(2,6-difluorophenyl)pyrimidin-5-yl]amino}benzoic acid, sodium salt | 1.87 |

As it can be seen for the table, the salt of the present invention present a higher solubility over the corresponding free acid.

Pharmaceutical Compositions

Pharmaceutical compositions according to the present invention comprise the salt of the invention or pharmaceutically acceptable solvate thereof and a pharmaceutically acceptable carrier.

The salt of the invention is useful in the treatment or prevention of diseases known to be susceptible to improvement by treatment with inhibitor of the dihydroorotate dehydrogenase. Such diseases include but are not limited to rheumatoid arthritis, psoriatic arthritis, ankylosing spondilytis, multiple sclerosis, Wegener's granulomatosis, systemic lupus erythematosus, psoriasis and sarcoidosis.

The salt of the invention may also be combined with other active compounds in the treatment of diseases known to be susceptible to improvement by treatment with an inhibitor of the dihydroorotate dehydrogenase.

The combinations of the invention can optionally comprise one or more additional active substances which are known to be useful in the treatment of autoimmune diseases, immune and inflammatory diseases, destructive bone disorders, malignant neoplastic diseases, angiogenic-related disorders, viral diseases, and infectious diseases such as (a) Anti-TNF-alpha monoclonal antibodies such as Infliximab, Certolizumab pegol, Golimumab, Adalimumab and AME-527 from Applied Molecular Evolution, (b) Antimetabolite compounds such as Mizoribine, Cyclophosphamide and Azathiopirine, (c) Calcineurin (PP-2B) Inhibitors/INS Expression Inhibitors such as cyclosporine A, Tacrolimus and ISA-247 from Isotechnika, (d) Cyclooxygenase Inhibitors such as Aceclofenac, Diclofenac, Celecoxib, Rofecoxib, Etoricoxib, Valdecoxib, Lumiracoxib, Cimicoxib and LAS-34475 from Laboratorios Almirall, S.A., (e) TNF-alpha Antagonists such as Etanercept, Lenercept, Onercept and Pegsunercept, (f) NF-kappaB (NFKB) Activation Inhibitors such as Sulfasalazine and Iguratimod, (g) IL-1 Receptor Antagonists such as Anakinra and AMG-719 from Amgen, (h) Dihydrofolate Reductase (DHFR) Inhibitors such as Methotrexate, Aminopterin and CH-1504 from Chelsea, (i) Inhibitors of Inosine 5'-Monophosphate Dehydrogenase (IMPDH) such as Mizoribine, Ribavirin, Tiazofurin, Amitivir, Mycophenolate mofetil, Ribamidine and Merimepodib, (j) Glucocorticoids such as Prednisolone, Methylprednisolone, Dexamethasone, Cortisol, Hydrocortisone, Triamcinolone acetonide, Fluocinolone acetonide, Fluocinonide, Clocortolone pivalate, Hydrocortisone aceponate, Methylprednisolone suleptanate, Betamethasone butyrate propionate, Deltacortisone, Deltadehydrocortisone, Prednisone, Dexamethasone sodium phosphate, Triamcinolone, Betamethasone valerate, Betamethasone, Hydrocortisone sodium succinate, Prednisolone sodium phosphate, Hydrocortisone probutate and Difluprednate, (k) Anti-CD20 monoclonal antibodies such as Rituximab, Ofatumumab, Ocrelizumab and TRU-015 from Trubion Pharmaceuticals, (l) B-targeted cell therapies such as BLYSS, BAFF, TACI-Ig and APRIL, (m) p38 Inhibitors such as AMG-548 (from Amgen), ARRY-797 (from Array Biopharma), Chlormethiazole edisylate, Doramapimod, PS-540446 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06 (all from Pfizer), RWJ-67657 (from R. W. Johnson), RO-3201195, RO-4402257 (all from Roche), AVE-9940 (from Aventis), SCIO-323, SCID-469 (all from Scios), TA-5493 (from Tanabe Seiyaku), and VX-745, VX-702 (all from Vertex) and the compounds claimed or described in Spanish patent applications numbers ES2303758 and ES2301380, (n) JAK3 Inhibitors such as CP690550 (tasocitinib) from Pfizer, (o) Syk inhibitors such as R-112, R-406 and R-788 all from Rigel, (p) MEK inhibitors such as ARRY-142886, ARRY-438162 (all from Array Biopharma), AZD-6244 (from AstraZeneca), PD-098059, PD-0325901 (all from Pfizer), (q) P2X7 receptor antagonist such as AZD-9056 from AstraZeneca, (r) S1P1 agonists such as Fingolimod, CS-0777 from Sankyo and R-3477 from Actelion, (s) Anti-CD49 monoclonal antibodies such as Natalizumab, (t) Integrin Inhibitors such as Cilengitide, Firategrast, Valategrast hydrochloride, SB-273005, SB-683698 (all from Glaxo), HMR-1031 from Sanofi-Aventis, R-1295 from Roche, BMS-587101 from BMS and CDP-323 from UCB Celltech, (u) Anti-CD88 monoclonal antibodies such as Eculizumab and Pexelizumab, (v) IL-6 receptor antagonist such as CBP-1011 from InKine and C-326 from Amgen, (w) Anti IL-6 monoclonal antibodies such as Elsilimomab, CNTO-328 from Centocor and VX-30 from Vaccinex, (x) Anti-CD152 monoclonal antibodies such as Ipilimumab and Ticilimumab, (y) Fusion proteins comprising the extracellular domain of human cytotoxic T-lymphocyte-associated antigen 4 (CTLA-4) linked to portions of human immunoglobulin G1 such as Abatacept, (z) Agents useful in the treatment of bone disorders such as Bisphosphonates such as Tiludronate disodium, Clodronate disodium, Disodium pamidronate, Etidronate disodium, Xydiphone (K, Na salt), Alendronate sodium, Neridronate, Dimethyl-APD, Olpadronic acid sodium salt, Minodronic acid, Apomine, Ibandronate sodium hydrate and Risedronate sodium, (aa) VEGF Try kinase inhibitors such as Pegaptanib octasodium, Vatalanib succinate, Sorafenib, Vandetanib, Sunitinib malate, Cediranib, Pazopanib hydrochloride and AE-941 from AEterna Zentaris, (bb) Other compounds efficacious in autoimmune diseases such as Gold salts, hydroxycloroquinine, Penicilamine, K-832, SMP114 and AD452, (cc) Purine-Nucleoside phosphorylase inhibitors such as Forodesine hydrochloride, R-3421 from Albert Einstein College of Medicine, CI-972 and CI-1000 both from Pfizer, (dd) Anti-RANKL monoclonal antibodies such as Denosumab, (ee) Anti-CD25 monoclonal antibodies such as Inolimomab, Dacliximab, Basiliximab and LMB-2 from the US National Cancer Institute, (ff) Histone Deacetylase (HDAC) Inhibitors such as Divalproex sodium, Acetyldinaline, Depsipeptide, Sodium butyrate, Sodium phenylbutyrate, Vorinostat, MS-27-275 from Mitsui, Valproic acid, Pyroxamide, Tributyrin, PX-105684 from TopoTarget, MG-0103 from MethylGene, G2M-777 from TopoTarget and CG-781 from Celera, (gg) Anti colony-stimulating factor (GM-CSF) monoclonal antibodies such as KB-002 from KaloBios, (hh) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex, (ii) Immunomodulators suchs as BG-12 (fumaric acid derivative) from Biogen Idec/Fumapharm AG; laquinimod (Teva and Active Biotech) or glatiramer acetate (Teva), and (jj) Adenosine aminohydrolase inhibitors such as Cladribine from Merck Serono.

When the salt of the invention is used for the treatment of rheumatoid arthritis, psoriatic arthritis, ankylosing spondilytis, multiple sclerosis, Wegener's granulomatosis, systemic lupus erythematosus, psoriasis and sarcoidosis it may be advantageous to use them in combination with other active compounds known to be useful in the treatment of such diseases such as rheumatoid arthritis, psoriatic arthritis, ankylosing spondilytis, multiple sclerosis, Wegener's granulomatosis, systemic lupus erythematosus, psoriasis and sarcoidosis.

Particularly preferred actives to be combined with the salt of the invention for treating or preventing rheumatoid arthritis, psoriatic arthritis, ankylosing spondilytis, multiple sclerosis, Wegener's granulomatosis, systemic lupus erythematosus, psoriasis or sarcoidosis are (a) Anti-TNF-alpha monoclonal antibodies such as Infliximab, Certolizumab pegol, Golimumab, Adalimumab and AME-527 from Applied Molecular Evolution, (b) TNF-alpha Antagonists such as Etanercept, Lenercept, Onercept and Pegsunercept, (c) Calcineurin (PP-2B) Inhibitors/INS Expression Inhibitors such as cyclosporine A, Tacrolimus and ISA-247 from Isotechnika, (d) IL-1 Receptor Antagonists such as Anakinra and AMG-719 from Amgen, (e) Anti-CD20 monoclonal antibodies such as Rituximab, Ofatumumab, Ocrelizumab and TRU-015 from Trubion Pharmaceuticals, (f) p38 Inhibitors such as AMG-548 (from Amgen), ARRY-797 (from Array Biopharma), Chlormethiazole edisylate, Doramapimod, PS-540446 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06 (all from Pfizer), RWJ-67657 (from R. W. Johnson), RO-3201195, RO-4402257 (all from Roche), AVE-9940 (from Aventis), SCIO-323, SCID-469 (all from Scios), TA-5493 (from Tanabe Seiyaku), and VX-745, VX-702 (all from Vertex) and the compounds claimed or described in Spanish patent applications numbers ES2303758 and ES2301380, (g) NF-kappaB (NFKB) Activation Inhibitors such as Sulfasalazine and Iguratimod, (h) Dihydrofolate Reductase (DHFR) Inhibitors such as Methotrexate, Aminopterin and CH-1504 from Chelsea, (n) JAK3 Inhibitors such as CP690550 (tasocitinib) from Pfizer, (p) MEK inhibitors such as ARRY-142886, ARRY-438162 (all from Array Biopharma), AZD-6244 (from AstraZeneca), PD-098059, PD-0325901 (all from Pfizer), (r) S1P1 agonists such as Fingolimod, CS-0777 from Sankyo and R-3477 from Actelion, (hh) Interferons comprising Interferon beta 1a such as Avonex from Biogen Idec, CinnoVex from CinnaGen and Rebif from EMD Serono, and Interferon beta 1b such as Betaferon from Schering and Betaseron from Berlex, (ii) Immunomodulators suchs as BG-12 (fumaric acid derivative) from Biogen Idec/Fumapharm AG and (jj) Adenosine aminohydrolase inhibitors such as Cladribine from Merck Serono.

The combinations of the invention may be used in the treatment of disorders which are susceptible to amelioration by inhibition of the dihydroorotate dehydrogenase. Thus, the present application encompasses methods of treatment of these disorders, as well as the use of the combinations of the invention in the manufacture of a medicament for the treatment of these disorders.

Preferred examples of such disorders are rheumatoid arthritis, psoriatic arthritis, ankylosing spondilytis, multiple sclerosis, Wegener's granulomatosis, systemic lupus erythematosus, psoriasis and sarcoidosis, more preferably rheumatoid arthritis, psoriatic arthritis and psoriasis and most preferably rheumatoid arthritis.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the salt of the invention, and the other optional active compounds may be administered together in the same pharmaceutical composition or in different compositions intended for separate, simultaneous, concomitant or sequential administration by the same or a different route.

One execution of the present invention consists of a kit of parts comprising the salt of the invention together with instructions for simultaneous, concurrent, separate or sequential use in combination with another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

Another execution of the present invention consists of a package comprising the salt of the invention and another active compound useful in the treatment of rheumatoid arthritis, psoriatic arthritis, ankylosing spondilytis, multiple sclerosis, Wegener's granulomatosis, systemic lupus erythematosus, psoriasis and sarcoidosis.

The pharmaceutical formulations may conveniently be presented in unit dosage form and may be prepared by any of the methods well known in the art of pharmacy.

Formulations of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 μg and 150 μg of each therapeutically active ingredient. Alternatively, the active ingredient (s) may be presented without excipients.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Effective doses are normally in the range of 2-2000 mg of active ingredient per day. Daily dosage may be administered in one or more treatments, preferably from 1 to 4 treatments, per day. Preferably, the active ingredients are administered once or twice a day.

When combinations of actives are used, it is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The following preparations forms are cited as composition (formulation) examples:

Composition Example 1

50,000 capsules, each containing 100 mg 5-cyclopropyl-2-{[2-(2,6-difluorophenyl)pyrimidin-5-yl]amino}benzoic acid, sodium salt (active ingredient), were prepared according to the following formulation:

| | |
|---|---|
| Active ingredient | 5 Kg |
| Lactose monohydrate | 10 Kg |
| Colloidal silicon dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 tablets, each containing 50 mg of 5-cyclopropyl-2-{[2-(2,6-difluorophenyl)pyrimidin-5-yl]amino}benzoic acid, sodium salt (active ingredient), were prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:

1. A crystalline sodium salt of 5-cyclopropyl-2-{[2-(2,6-difluorophenyl)pyrimidin-5-yl]amino}benzoic acid.

2. A pharmaceutical composition comprising the crystalline sodium salt of claim 1 and a pharmaceutically acceptable carrier.

3. The pharmaceutical composition according to claim 2, wherein the composition further comprises at least one other therapeutic agent.

4. The pharmaceutical composition of claim 3, wherein the at least one other therapeutic agent is selected from:
  a) Anti-TNF-alpha monoclonal antibodies,
  b) TNF-alpha Antagonists,
  c) Calcineurin (PP-2B) Inhibitors/INS Expression Inhibitors,
  d) IL-1 Receptor Antagonists,
  e) Anti-CD20 monoclonal antibodies,
  f) p38 Inhibitors,
  g) NF-kappaB (NFKB) Activation Inhibitors,
  h) Dihydrofolate Reductase (DHFR) Inhibitors,
  i) JAK3 Inhibitors,
  j) MEK inhibitors,
  k) S1P1 agonists,
  l) Interferons comprising Interferon beta 1a,
  n) Adenosine aminohydrolase inhibitors.

5. A combination comprising the crystalline sodium salt of claim 1 and at least one other therapeutic agent selected from:
  a) Anti-TNF-alpha monoclonal antibodies,
  b) TNF-alpha Antagonists,
  c) Calcineurin (PP-2B) Inhibitors/INS Expression Inhibitors,
  d) IL-1 Receptor Antagonists,
  e) Anti-CD20 monoclonal antibodies,
  f) p38 Inhibitors,
  g) NF-kappaB (NFKB) Activation Inhibitors,
  h) Dihydrofolate Reductase (DHFR) Inhibitors,
  i) JAK3 Inhibitors,
  j) MEK inhibitors,
  k) S1P1 agonists,
  l) Interferons comprising Interferon beta 1a,
  m) Immunomodulators, and
  n) Adenosine aminohydrolase inhibitors.

* * * * *